(12) United States Patent
Hazut et al.

(10) Patent No.: US 7,905,854 B2
(45) Date of Patent: Mar. 15, 2011

(54) APPARATUS AND METHOD FOR REMOVING PIGMENTS FROM A PIGMENTED SECTION OF SKIN

(75) Inventors: Aharon Hazut, Emek HaYarden (IL); Golan Fredi Hok, Hazor HaGlilit (IL)

(73) Assignee: Hawk Medical Technologies Ltd., Hod Hasharon (IL)

( * ) Notice: Subject to any disclaimer, the term of this patent is extended or adjusted under 35 U.S.C. 154(b) by 765 days.

(21) Appl. No.: 10/569,525

(22) PCT Filed: Aug. 30, 2004

(86) PCT No.: PCT/IL2004/000784
§ 371 (c)(1),
(2), (4) Date: Oct. 12, 2006

(87) PCT Pub. No.: WO2005/020828
PCT Pub. Date: Mar. 10, 2005

(65) Prior Publication Data
US 2007/0156095 A1 Jul. 5, 2007

(30) Foreign Application Priority Data
Sep. 1, 2003 (IL) .......................................... 157696

(51) Int. Cl.
A61B 17/20 (2006.01)
A61M 1/00 (2006.01)
(52) U.S. Cl. ........................................ 604/22; 604/28
(58) Field of Classification Search ............... 606/11, 606/9
See application file for complete search history.

(56) References Cited

U.S. PATENT DOCUMENTS

| | | | |
|---|---|---|---|
| 4,588,400 A | 5/1986 | Ring et al. | |
| 4,858,604 A * | 8/1989 | Konishi | 602/57 |
| 5,019,596 A | 5/1991 | Reiner et al. | |
| 5,244,920 A | 9/1993 | Reiner et al. | |
| 5,271,943 A | 12/1993 | Bogart et al. | |
| 5,401,242 A * | 3/1995 | Yacowitz | 604/48 |
| 5,423,736 A | 6/1995 | Cartmell et al. | |
| 6,251,121 B1 | 6/2001 | Saadat | |
| 6,375,977 B1 | 4/2002 | Auguste et al. | |
| 6,607,513 B1 | 8/2003 | Lastovich et al. | |
| 6,689,095 B1 | 2/2004 | Garitano et al. | |
| 6,692,456 B1 | 2/2004 | Eppstein et al. | |

(Continued)

FOREIGN PATENT DOCUMENTS
FR 983 602 A 6/1951
(Continued)

OTHER PUBLICATIONS
International Search Report PCT/IL2004/000784.
(Continued)

*Primary Examiner* — Nicholas D Lucchesi
*Assistant Examiner* — Pritesh Patel
(74) *Attorney, Agent, or Firm* — Martin Fleit; Paul D. Bianco; Fleit Gibbons Gutman Bongini & Bianco, PL

(57) ABSTRACT

An apparatus for removing a pigmented section of skin, comprises a) a skin puncturing device; b) an array of one or more needles connected to said device for puncturing the skin at said pigmented section; and c) a mediating member attached to said device and to suction means, for allowing said suction means to collect the mixture of the pigments with the cellular fluids at said punctured section of the skin.

19 Claims, 14 Drawing Sheets

U.S. PATENT DOCUMENTS

| | | | |
|---|---|---|---|
| 6,743,211 B1 * | 6/2004 | Prausnitz et al. | 604/239 |
| 7,012,096 B2 | 3/2006 | Dosch et al. | |
| 7,314,470 B2 * | 1/2008 | Malodobry | 606/131 |
| 2002/0138049 A1 | 9/2002 | Allen et al. | |
| 2002/0183688 A1 | 12/2002 | Lastovich et al. | |
| 2004/0001878 A1 | 1/2004 | DeBusk et al. | |
| 2004/0111107 A1 | 6/2004 | Malodobry | |
| 2004/0158196 A1 | 8/2004 | Garitano et al. | |
| 2006/0142708 A1 | 6/2006 | Hazut et al. | |
| 2007/0156095 A1 | 7/2007 | Hazut et al. | |

FOREIGN PATENT DOCUMENTS

| | | |
|---|---|---|
| GB | 2 234 420 A | 2/1991 |
| JP | 2001293095 A | 10/2001 |
| SU | 1109168 A | 8/1984 |
| WO | 9964580 | 12/1999 |
| WO | WO 00/64514 A | 11/2000 |
| WO | 0076411 A2 | 12/2000 |
| WO | WO 00/74767 A | 12/2000 |
| WO | WO 02/36027 A | 5/2002 |
| WO | 2004/107995 | 12/2004 |

OTHER PUBLICATIONS

International Preliminary Report on Patentability PCT/IL2004/000784.
Written Opinion of the International Search Authority PCT/IL2004/000784.
Office Action dated Jul. 20, 2010 for U.S. Appl. No. 10/560,063.
International Search Report published Jan. 27, 2005 for International Application No. PCT/IL2004/0497, filed Jun. 10, 2004.
Written Opinion published Dec. 10, 2005 for International Application No. PCT/IL2004/0497, filed Jun. 10, 2004.
International Preliminary Report on Patentability published Dec. 10, 2005 for International Application No. PCT/IL2004/0497, filed Jun. 10, 2004.
Eddy M. Van Der Velden et al, Tattoo Removal: Tannic Acid Method of Variot, Pharmacology and Terapeutics, pp. 376-380, vol. 5, No. 5, May 1993.
Gary H. Manchester, Tattoo Removal, The Western Journal of Medicine, pp. 10-12, vol. 118, Mar. 1973.
"Tattoo Removal". http://patient-info.com/tattoo.htm. Copyright 2000. p. 3—Salabrasion.
Material Safety Data Sheet (MSDS) for Sodium Chloride ACS Reagent sold by Sigma-Aldrich, Feb. 1, 2006.
Material Safety Data Sheet (MSDS) for RN-Free Buffer (5M NaC1) sold by Ambion, Inc., Jan. 10, 2006.
Takesue, M, Aichi Gakuin Daigaku Shigakkai Shi, 27(1): 277-316, 1989, Effect of Caffeine on Wound Healing of the Rat Gingiva, abstract.
Office Action dated Oct. 26, 2009 in U.S. Appl. No. 10/560,063.
Final Office Action dated Mar. 16, 2009 in U.S. Appl. No. 10/560,063.
Final Office Action dated Dec. 24, 2008 in U.S. Appl. No. 10/560,063.
Final Office Action dated Oct. 18, 2007 in U.S. Appl. No. 10/560,063.
Office Action dated Feb. 26, 2007 in U.S. Appl. No. 10/560,063.
Office Action dated Apr. 16, 2008 in U.S. Appl. No. 10/560,063.
Taylor et al, Light and Electron Microscopic . . . , J Investigative Dermatology, p. 131-36, 1991.
www.healthylivinganswers.com/skin-care/, Feb. 26, 2010m "layers of the skin-epidermis-dermis-hypodermis".

* cited by examiner

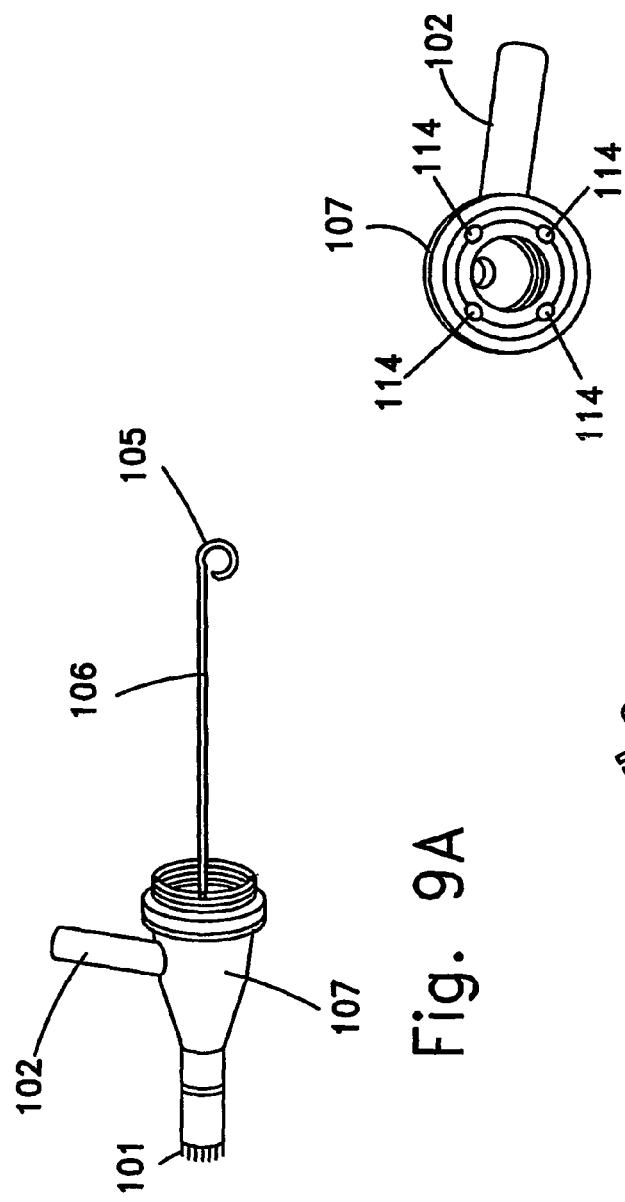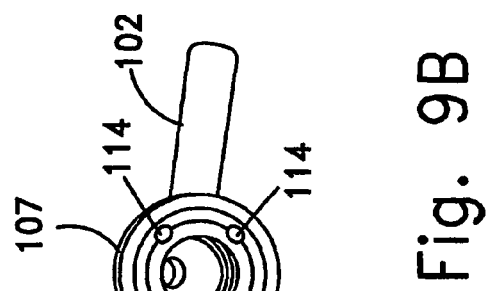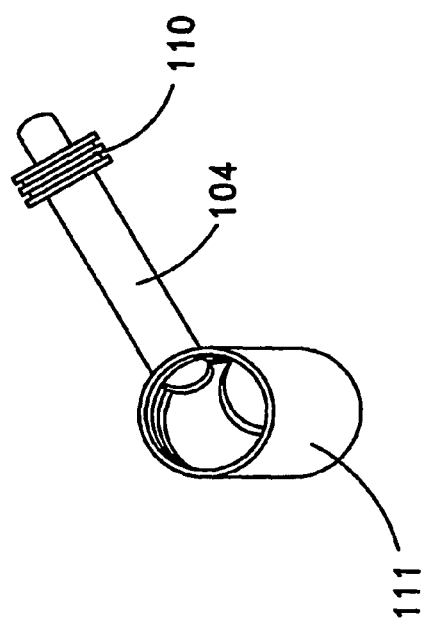

APPARATUS AND METHOD FOR REMOVING PIGMENTS FROM A PIGMENTED SECTION OF SKIN

FIELD OF THE INVENTION

The present invention relates to the field of pigment removal. More particularly, the invention relates to an apparatus and to a method for removing a pigmented section of skin, particularly a tattoo.

BACKGROUND OF THE INVENTION

Tattoos are created by injecting ink into the skin. Today, in most cases, the injection of the ink is done by one or more solid needles which are attached to a device (referred to hereinafter as "skin puncturing device"). Preferably, but not limitatively, the skin puncturing device is a hand-held device. The skin puncturing device moves the needle along the longitudinal axis of the device, similar to the movement of a needle in a sewing machine. Usually the skin puncturing device moves the needle at a rate of several vibrations per minute (e.g., the needles may puncture the skin at the rate of 50 to 3,000 times per minute). Prior to the penetration of the needle into the skin, the needle is dipped in a suitable solution which contains pigment (e.g., ink) and then this solution is sucked up through a suitable tube system of the skin puncturing device. After receiving the solution the skin puncturing device is used to puncture the top layer of the skin and injects insoluble, micrometer-sized particles of ink into the dermal layer of skin (i.e., dermis), preferably, about one millimeter deep. As a result, the ink is not located in the epidermis, but it infiltrates the cells in the dermis. Since the cells of the dermis are relatively fixed, the tattoo's ink remains at the dermis, thereby permanently tattooing the skin.

For a variety of reasons, there are people who wish to remove a tattoo (or other pigment) from their skin. However, because tattoos become an integral part of the cells in the dermis, removing them is not an easy task. In the prior art several methods for removing tattoos have been suggested, which, however are usually invasive; some methods even require surgery and may also be painful. Such known methods are:

Dermabrasion, wherein skin is "sanded" (i.e., abraded) to remove the surface which contains the tattoo;

Cryosurgery, wherein the area where the tattoo is located is frozen prior to its removal; and Excision, wherein the dermatologic surgeon removes the tattoo with a scalpel and closes the wound with stitches (In some cases involving large tattoos, a skin graft from another part of the body may be necessary).

However, such tattoo-removal methods are painful and may also create scars.

Other methods for tattoo removal use lasers. Lasers offer a bloodless alternative to the abovementioned methods and may also have fewer side effects. Each removal procedure is done in a single treatment, or in a series of treatments. Patients may or may not require topical or local anesthesia. Lasers remove tattoos by producing short pulses of intense light, which pass through the top layers of the skin and are then selectively absorbed by the tattoo pigment. This laser energy causes the tattoo pigment to be fragmented into smaller particles, which are then removed by the body's immune system. However, there is still a possibility that using a laser may cause scarring. Furthermore, it is difficult with a laser to remove pigments of yellow and green. Such colors selectively absorb laser light and can only be treated by selected lasers based on the pigment color. Moreover, there are side effects of laser procedures which may cause hyper pigmentation, or an abundance of color in the skin at the treatment site, and hypo pigmentation, where the treated area lacks normal skin color.

In addition, tattoo removal using each of the above methods is long and expensive.

All the methods described above have not yet provided satisfactory solutions to the problem of removing a pigmented section of skin by simple means.

It is an object of the present invention to provide a method for removing a pigmented section of skin while overcoming the drawbacks of the prior art.

It is another object of the present invention to provide a method for removing a pigmented section of skin at a relatively low cost.

Other objects and advantages of the invention will become apparent as the description proceeds.

SUMMARY OF THE INVENTION

The present invention relates to an apparatus for removing a pigmented section of skin, which comprises: (a) a skin puncturing device; (b) an array of one or more needles connected to said device for puncturing the skin at said pigmented section; and (c) a mediating system attached to said device and to suction means for allowing said suction means to collect the mixture of the pigments with the cellular fluids at said punctured section of skin, wherein said member is capable of creating an essentially isolated area above said punctured section of skin, which is suitable for puncturing and for suction of the area.

According to a preferred embodiment of the invention, the mediating system comprises a mediating member having one or more openings through which the suction means collects the mixture of the pigments with the cellular fluids and, optionally, with externally-injected materials.

According to a preferred embodiment of the invention, the mediating member further comprises means for attaching it to a source of a cleaning material, for applying the cleaning material onto the punctured skin, thereby cleaning the punctured area during the removal of the pigments from the pigmented section of the skin. Preferably, the means for attaching the mediating member to the source of a cleaning material are one or more openings through which the source of cleaning material delivers the cleaning material onto the punctured skin.

Preferably, the mediating system is attached to the skin puncturing device in such a way that the openings of the mediating member are located adjacent to the sharp edge of the array of needles.

According to another preferred embodiment of the present invention, the one or more needles are hollow. The hollow needles are provided with openings suitable to be connected to a source of cleaning material for applying the cleaning material onto the punctured skin, thereby cleaning the punctured area during the removal of the pigmented section of skin. The cleaning material may also consist of, or comprise as an additive, one or more antiseptic and/or disinfecting material.

Preferably, the cleaning material is a fluid, air under pressure or a combination of both fluid and air pressure.

Preferably, the mediating member is attached to the puncturing device with one or more screws.

According to a preferred embodiment of the invention, the skin puncturing device is an electric device for creating tattoos (i.e., a tattooing machine).

The present invention further relates to a method for removing a pigmented section of a skin, which comprises: a) providing a skin puncturing device which includes one or more needles and suction means; b) puncturing the skin at said pigmented section with said needles while said skin puncturing device contains no ink and performing suction (with said suction means), of the mixture of the pigments with the cellular fluids at said punctured section of the skin; c) optionally, providing a pad containing one or more materials capable of absorbing moisture from said mixture; and d) bandaging said punctured skin with said pad, thereby causing the pigment residue at said section to migrate from their location towards the outer layer of the skin.

According to a preferred embodiment of the present invention, the method further comprises applying (e.g., spraying) fluids on the punctured section of skin for cleaning said section.

According to another preferred embodiment of the present invention, the method further comprises bandaging the punctured skin with a pad containing one or more antiseptic materials for preventing infections.

According to a preferred embodiment of the invention the material applied to the pigments is saline.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein:

FIG. 9 shows some of the elements of the apparatus of FIG. 7 in perspective view;

DETAILED DESCRIPTION OF PREFERRED EMBODIMENTS

As stated above, the present invention relates to an apparatus for removing a pigmented section of a skin by puncturing the skin at the pigmented section of the skin and concurrently performing a suction of the mixture of the pigments with the cellular fluids (with or without externally added fluids) at the punctured section of the skin.

Figure 1:
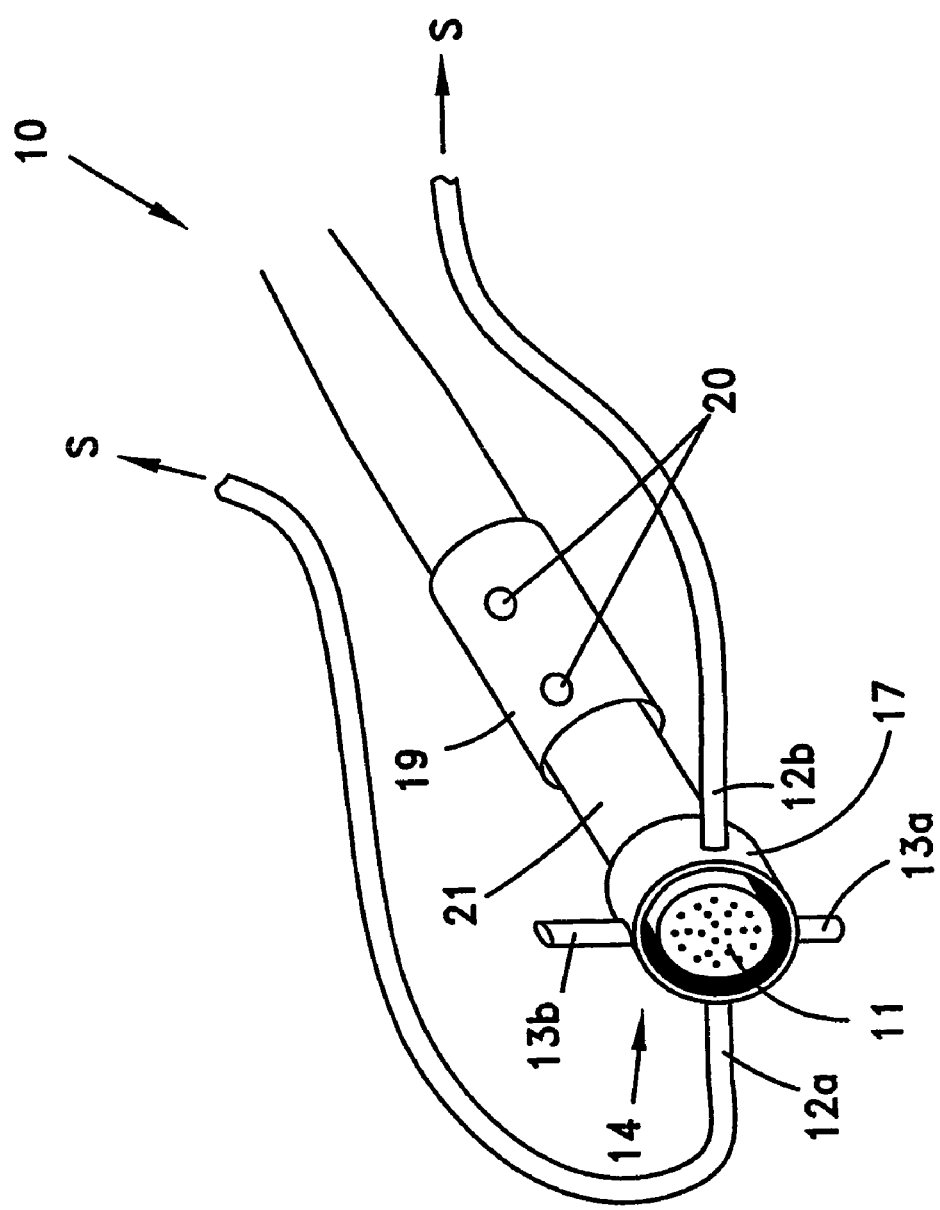
FIG. 1 schematically illustrates an apparatus for removing a pigmented section of a skin, according to a preferred embodiment of the present invention.
Figure 2A:
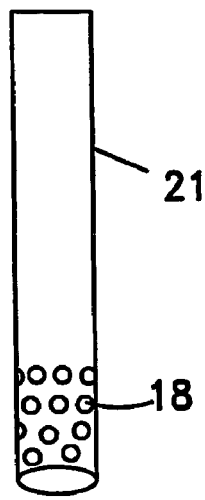
FIG. 2 schematically illustrates the components of the apparatus of FIG. 1.
Figure 2B:
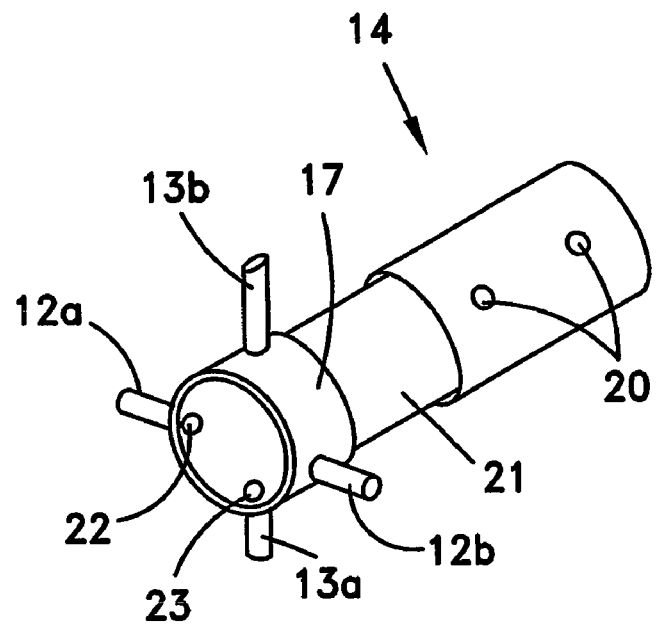
Figure 2C:
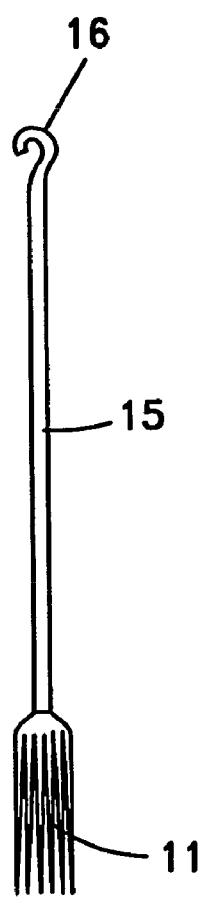

FIGS. 1 and 2 schematically illustrate the apparatus 10 for removing a pigmented section of a skin, according to a preferred embodiment of the present invention. Apparatus 10 comprises an array of one or more needles 11 (the tips of which are seen in the figure) for puncturing the skin at the pigmented section, and a mediating system 14.

Apparatus 10 operates when attached to a device which causes needles 11 to vibrate, such as a typical tattooing machine (i.e., skin puncturing device). Needles 11 can be attached to a skin puncturing device by any suitable method well known to a person skilled in the art of tattooing and not described herein in detail, for the sake of brevity, for example by rod 15 (FIG. 2) which has typical connecting means 16 suitable to be connected to the skin puncturing device and which is provided with the array of needles 11 at the other end.

Mediating system 14 is attached to the skin puncturing device and to suction means. Mediating system 14 comprises tube 21 and a mediating member 17. Member 17 is used for allowing the suction means to collect the mixture of the pigments with the cellular fluids at the punctured section of skin, wherein member 17 is capable of creating and essentially sealed cavity above the punctured section of skin.

Mediating member 17 has one or more openings, such as opening 22, through which the suction means collects the mixture of the pigments with the cellular fluids. Tube 21 of mediating system 14 is used for connecting system 14 to the skin puncturing device 30 (FIG. 3), used to actuate the needles. Tube 21 is provided with one or more openings 18, as shown in FIG. 2(a). Member 17 is attached to tube 21 (e.g., by one or more screws) adjacent to openings 18.

According to a preferred embodiment of the invention, the array of needles 11 is inserted within tube 21 of system 14 and thus opening 18 of tube 21 and openings 22 of member 14 are located adjacent to the edges of needles 11.

Figure 3:
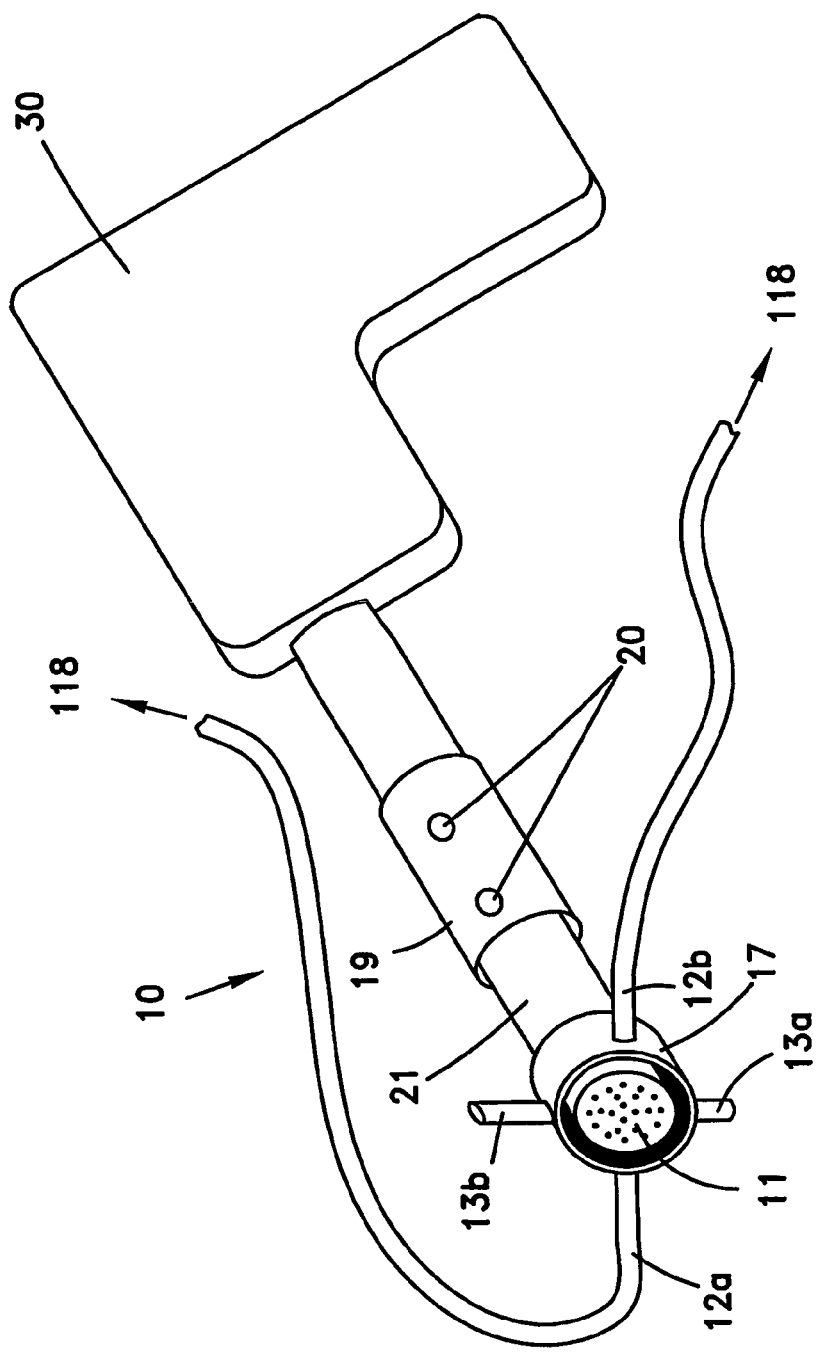
FIG. 3 schematically illustrates a skin puncturing device provided with the apparatus of FIG. 1.

Preferably, openings 22 of member 17 are suitable to be connected to a tubule 12a and 12b of suction means (not shown) for performing the suction operation. Tube 21 also comprises fastening means for attaching system 14 to the skin puncturing device 30 (FIG. 3). Preferably, but not limitatively, the fastening means are screws 20 and a ring 19. Of course, the fastening means can be any suitable means, which are well within the scope of a person skilled in the art.

According to a preferred embodiment of the invention member 17 is further provided with additional openings 23, suitable to be connected to tubules 13a and 13b, in turn connected to one or more sources of cleaning material(s) (not shown). The cleaning materials are used to clean the punctured area of skin of residues of blood, cellular fluids and pigments, during the removal treatment, by applying (e.g., by spraying) the cleaning material on the punctured skin, thereby cleaning the punctured area during the removal of the pigmented section of skin. For example, the cleaning material can be air under pressure, water or another fluid suitable to be sprayed onto a punctured human body. Of course, the cleaning material can be a combination of two or more materials, such as air pressure and water.

According to another preferred embodiment of the present invention, one or more of the needles are hollow. Each hollow needle has one or more openings suitable to be connected to a source of cleaning material for spraying the cleaning material onto the punctured skin, thereby cleaning the punctured area during the removal of the pigmented section of skin, or for injecting it therein. For instance, the cleaning material can be sprayed on the skin through the cavity along each hollow needle.

By employing the apparatus 10 of the present invention, removing a pigmented section of a skin, can be achieved as follows:

attaching apparatus 10 to a skin puncturing device;
puncturing the skin at said pigmented section with needles 11 while the skin puncturing device contains no ink; and
performing suction, with the suction means, of the mixture of the pigments with the cellular fluids at said punctured section of skin, (and, optionally, of any externally-added fluid) as described hereinabove.

Optionally, after completion of the puncturing of the skin at the pigmented section and completion of the suction operation, the treated section of skin can then be bandaged with a suitable adsorbing pad. The pad must contain one or more materials, such as saline, which will cause the pigment residue, at the punctured section, to migrate and to be absorbed into the outer layer of skin. Preferably, but not limitatively, the pad is an adsorbent pad able to absorb moisture from a mixture of tattoo ink and cellular fluid. Of course, the materials which will cause the pigments at the punctured section to migrate and to be absorbed into the outer layer of skin may be in the form of a solution, a solid material or a combination of both a solution and a solid material.

Preferably, after puncturing the area, a treatment for preventing infections should be provided for the skin in that area. Of course, the adsorbent pad may contain one or more antiseptic materials, such as Benzalkonium Chloride based cream (e.g., Bepanthen), Silver sulfadiazine based cream (e.g., Silverol) etc. Such antiseptic materials may also be applied separately. For example, the absorbent pad or other individual pads may contain pastes and/or creams known in the art, such as Vitamerfen, Bepanthen, Silverol and the like. Alternatively, the antiseptic based cream may be applied directly to the treated area and covered by a pad.

Preferably—but not limitatively, the skin puncturing device is a typical electric device for creating tattoos provided with the apparatus 10 of the present invention.

According to a preferred embodiment of the present invention, the apparatus 10 includes one or more needles 11, such as the one used for creating tattoos. Preferably, after attaching apparatus 10 to a skin puncturing device, the user may operate this device in the same way as that for creating tattoos, but without using ink. As an option, an aqueous solution or other material that does not contain pigments may be used (i.e., injected to the punctured area) instead of the ink, thereby the pigments may be further diluted and may be sucked away more easily.

In typical puncturing devices the penetrating depth of needles 11 into the skin is adjustable. Preferably, but not limitatively, the needles 11 do not penetrate beyond the hypodermis layer of the skin and thus no further damage to the skin is created while using the apparatus 10 of the present invention.

This invention can typically be used with any existing tattooing device, such as those produced by the firm of Lauro Paolini, Italy. For example, FIG. 3 schematically illustrates a typical tattooing device 30 provided with the apparatus 10 of FIG. 1, for removing pigmented sections of skin. Numeral 118 indicates a connection to suction means (not shown).

Figure 4:
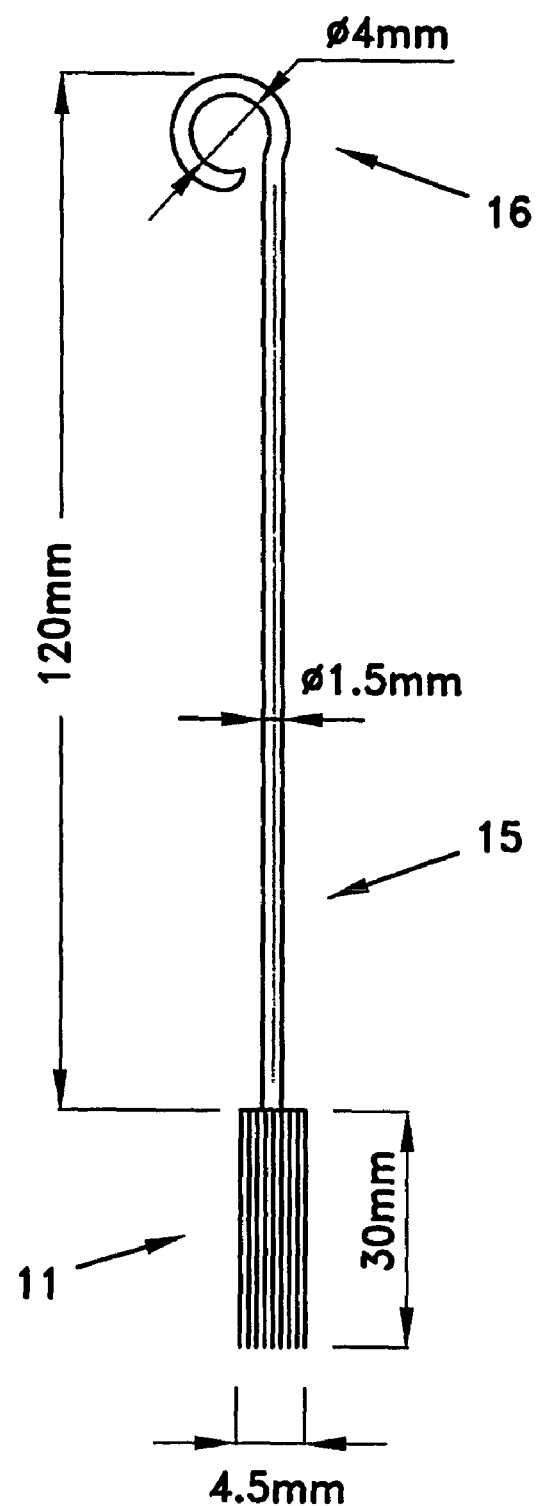
FIG. 4 illustrates the actual dimensions of an array of needles.

FIG. 4 shows an example of actual dimensions of a rod 15, according to a particular embodiment of the invention. All dimensions are given in millimeters.

Figure 5:
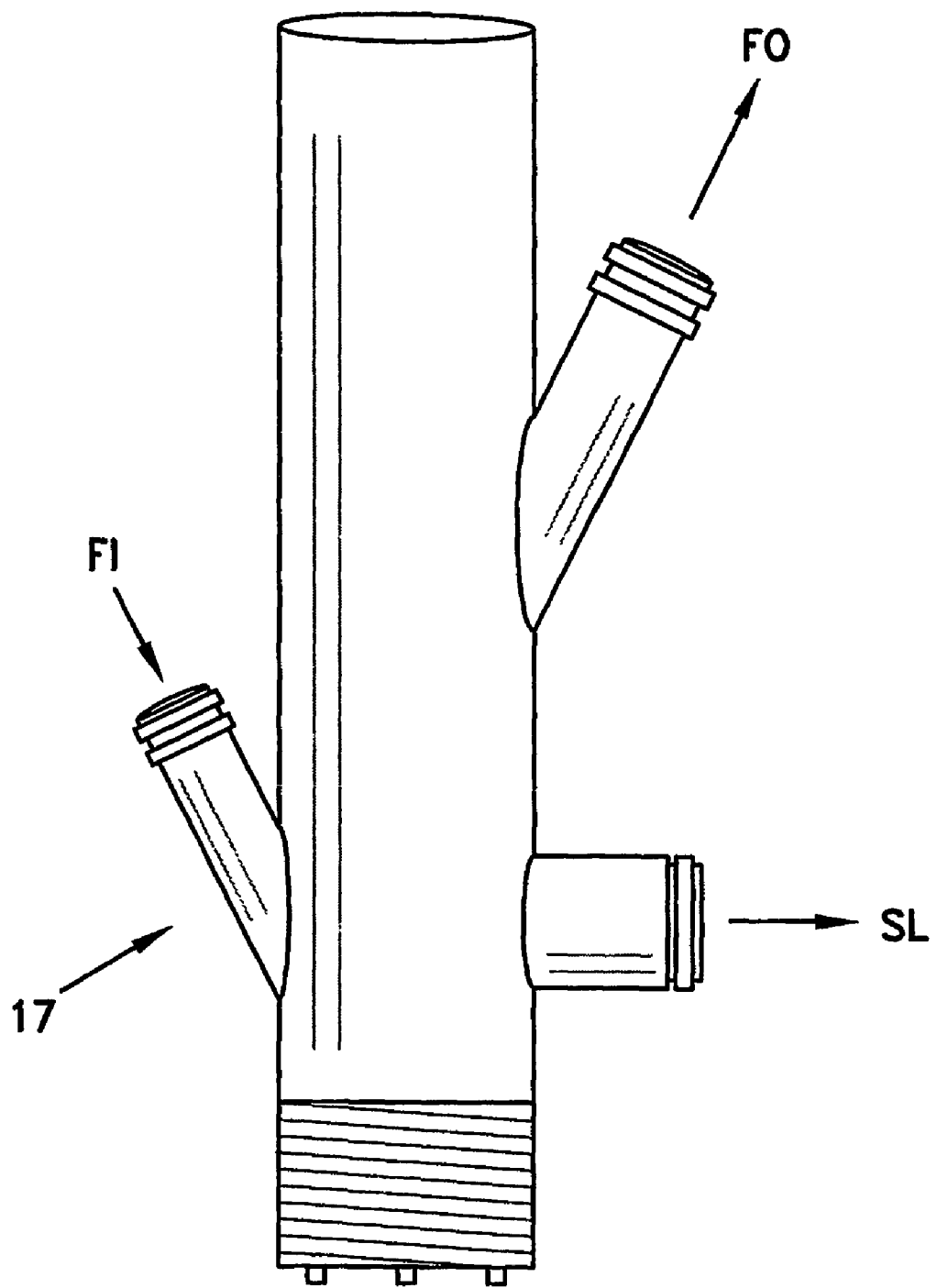
FIG. 5 schematically illustrates a mediating member according to an alternative preferred embodiment of the invention.

FIG. 5 schematically shows a particular arrangement for the treatment of fluids of means 17. SL denotes a port through which cellular fluids can be removed by suctions. If an additional fluid (e.g., warm saline or sterile water) is employed, it is supplied, in this particular embodiment, via port FI and then removed, together with debris from the treatment area, via port FO.

Figure 6:
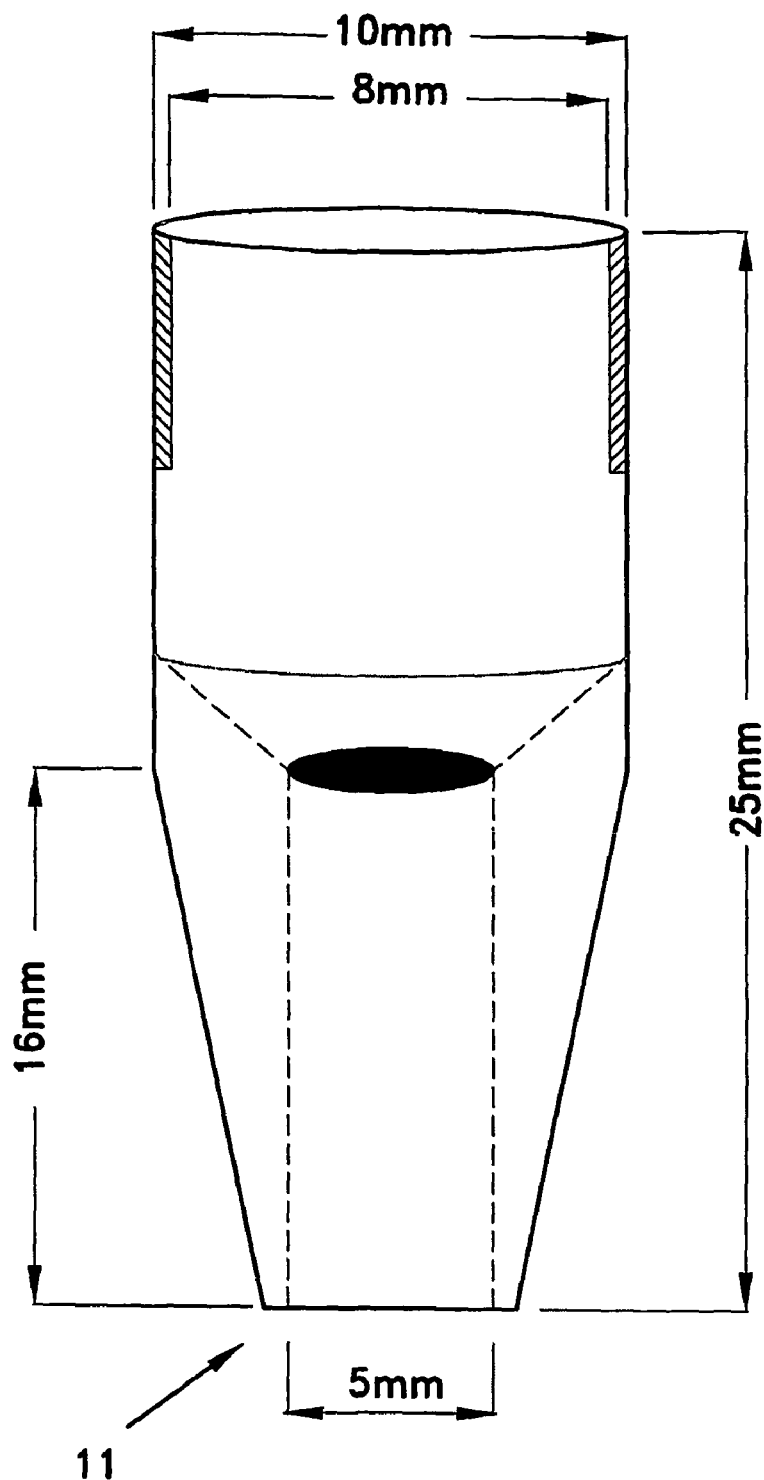
FIG. 6 illustrates the actual dimensions of the tip of an apparatus, according to a preferred embodiment of the invention.

FIG. 6 schematically shows a head for mediating element 17, through which needles 11 operate (not shown) via an opening of about 5 mm in diameter. The whole length of the head is, in this embodiment, only 25 mm. Thus, the small dimensions of a typical apparatus according to the invention can be appreciated through the indicative dimensions provided in the figure.

Figure 7:
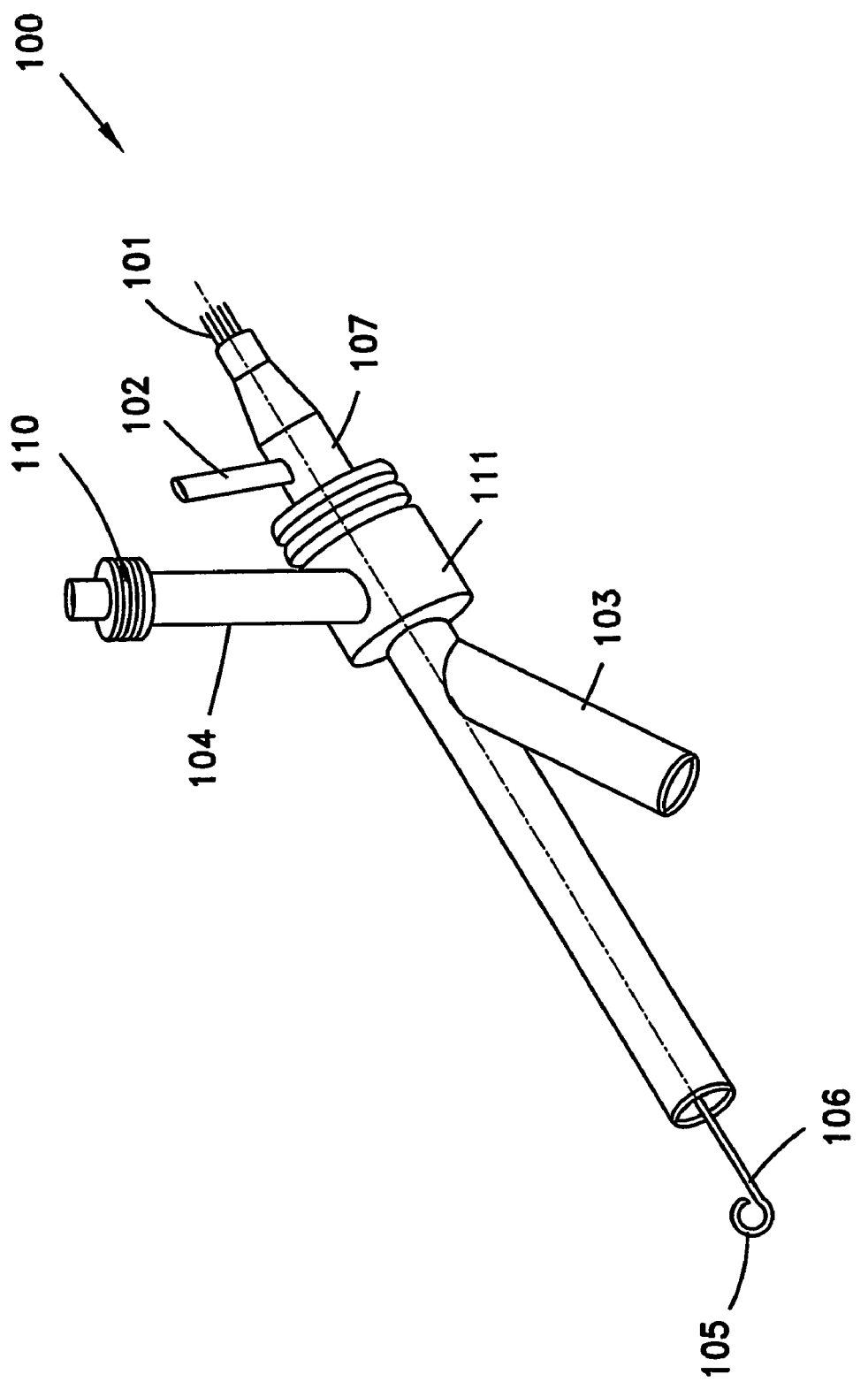
FIG. 7 schematically shows an apparatus for removing pigments from a pigmented section of skin, constructed according to another preferred embodiment of the invention.

FIG. 7 schematically shows an apparatus 100 for removing pigments from a pigmented section of skin, constructed according to another preferred embodiment of the invention. Apparatus 100 comprises an array of one or more needles 101 for puncturing the skin, a rod 106 to which the array of needles 101 is connected, a first drainage 102 for evacuating the mixture of the pigments and cellular fluids, a second drainage 103 for evacuating extra fluids and a mediator 111 for allowing to connect an external device for supplying cleaning materials, such as water or another fluid suitable to be sprayed on a punctured human body.

Figure 8:
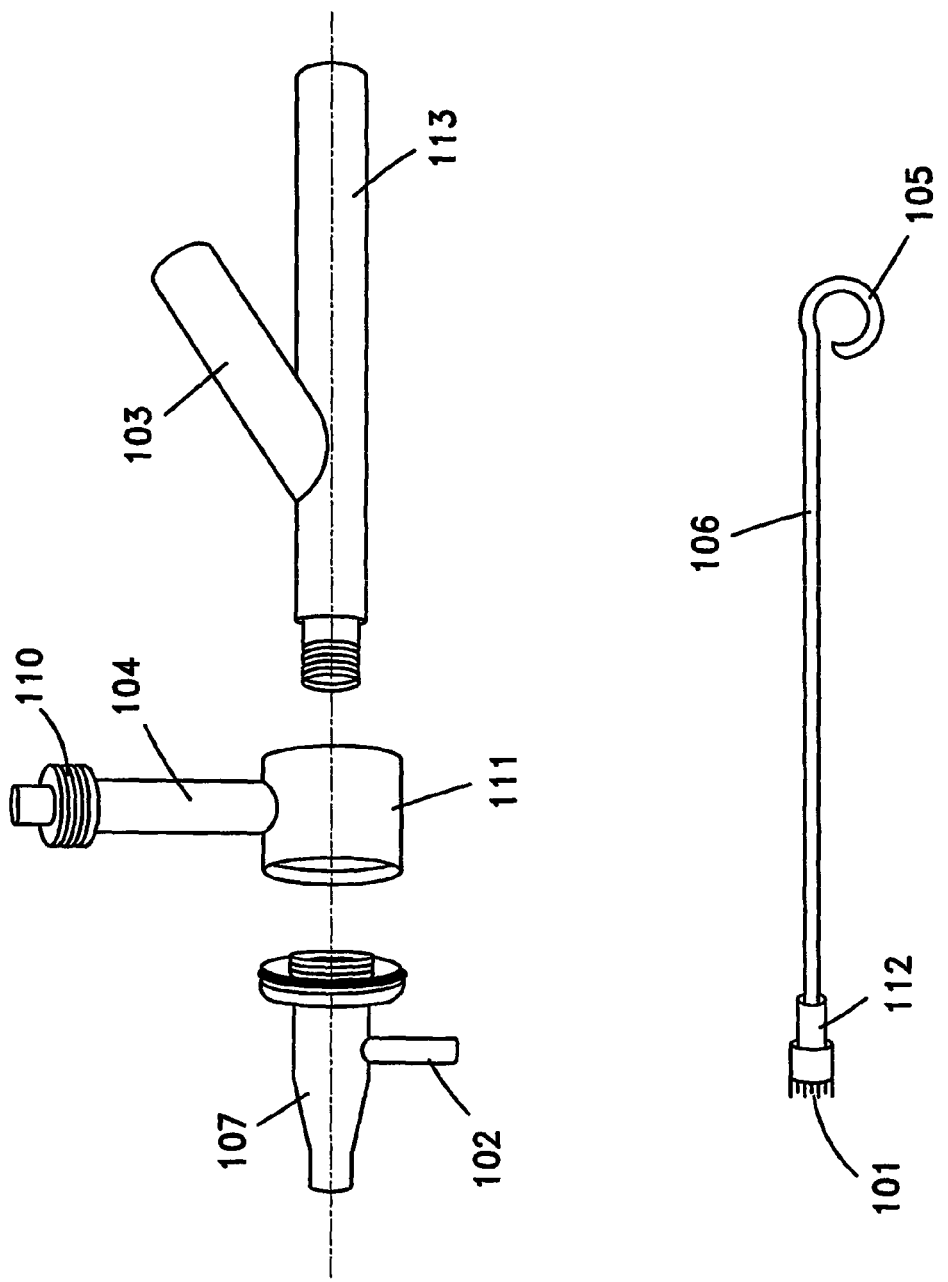
FIG. 8 schematically illustrates the different components of the apparatus of FIG. 7.

FIG. 8 schematically illustrates the different components of apparatus 100, according to one preferred embodiment of the invention. This figure shows the four different components of apparatus 100. Component (a) is the rod 106, which is provided at one end with the array of needles 101 and at the other end with a hook 105 for connecting apparatus 100 to a vibration unit (e.g., the tattooing gun 113 of FIG. 10). Component (b) comprises the second drainage 103 connected to a hollow cylindrical body 113 through which rod 106 is inserted and used to move or vibrate during the removal operation. Component (c) is the mediator 111. Mediator 11 comprises a tube 104 for leading the fluids or cleaning materials into apparatus 100 and fastening means 110 for connecting an external source of cleaning material to apparatus 100. FIG. 9 (c) is a perspective view of mediator 111. Component (d) is a conical element 107, which houses needles 101. Conical element 107 also comprises the first drainage 102. Component (b), (c) and (d) are connected to one another, while component (a) is inserted into components (b) through (d). FIG. 9 (a) show rod 106 in its inserted position within conical element 107.

FIG. 9 (b) is a schematic top view of conical element 107. This figure shows channels 114 which are used to lead the cleaning material towards the array of needles 101.

Figure 10:
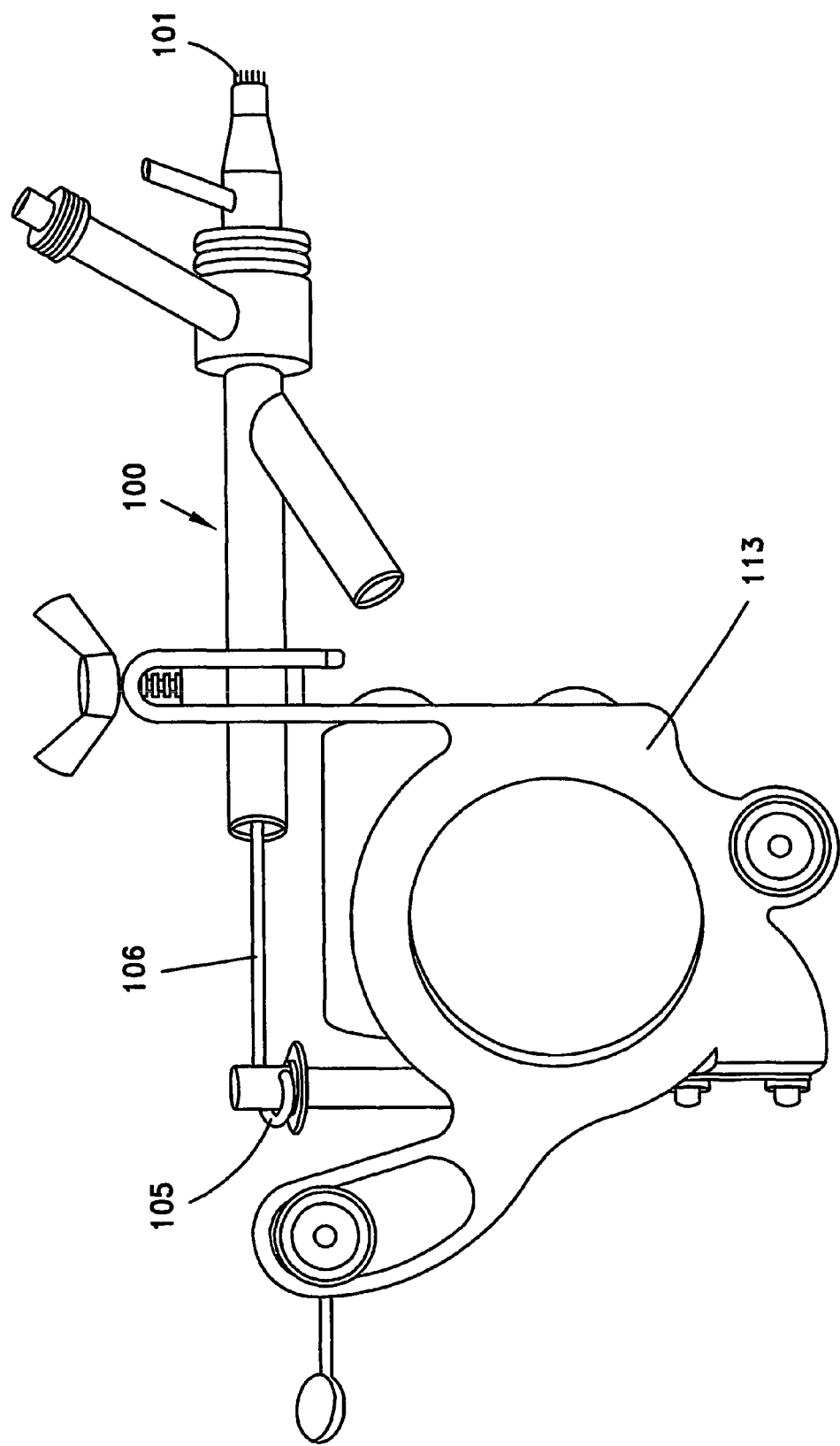
FIG. 10 schematically shows the apparatus of FIG. 7, in working position when attached to a typical tattooing gun.

FIG. 10 schematically shows apparatus 100 attached to a typical tattooing gun 113.

Figure 11:
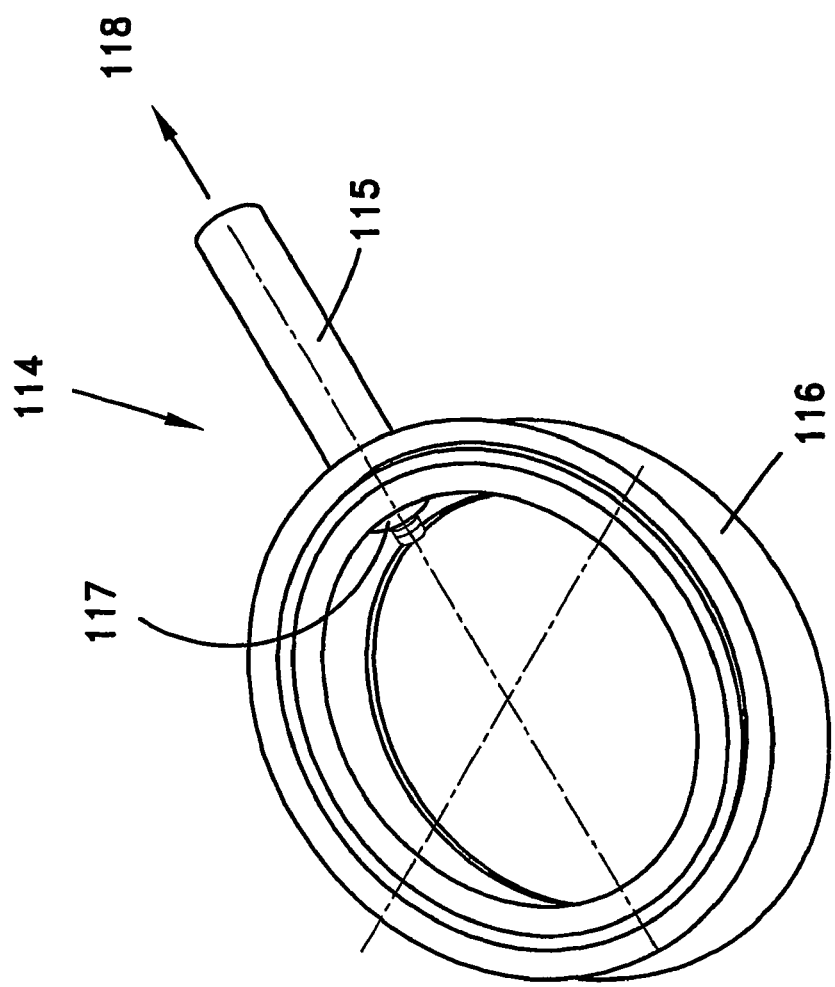
FIG. 11 schematically shows a boundary element used for limiting the spreading of the mixture of cellular fluids and pigments.

FIG. 11 schematically shows a boundary element 114 used for limiting the spreading of the mixture of cellular fluids and pigments. Element 114 comprises a boundary ring 116 for limiting the spreading area and a tube 115 for evacuating the mixture. Ring 116 is provided with a hole 117, through which the mixture is sucked into tube 115. Tube 115 can be connected to external suction means for evacuating the mixture from the punctured area. Opening 118 is the connection to the suction device.

Figure 12:
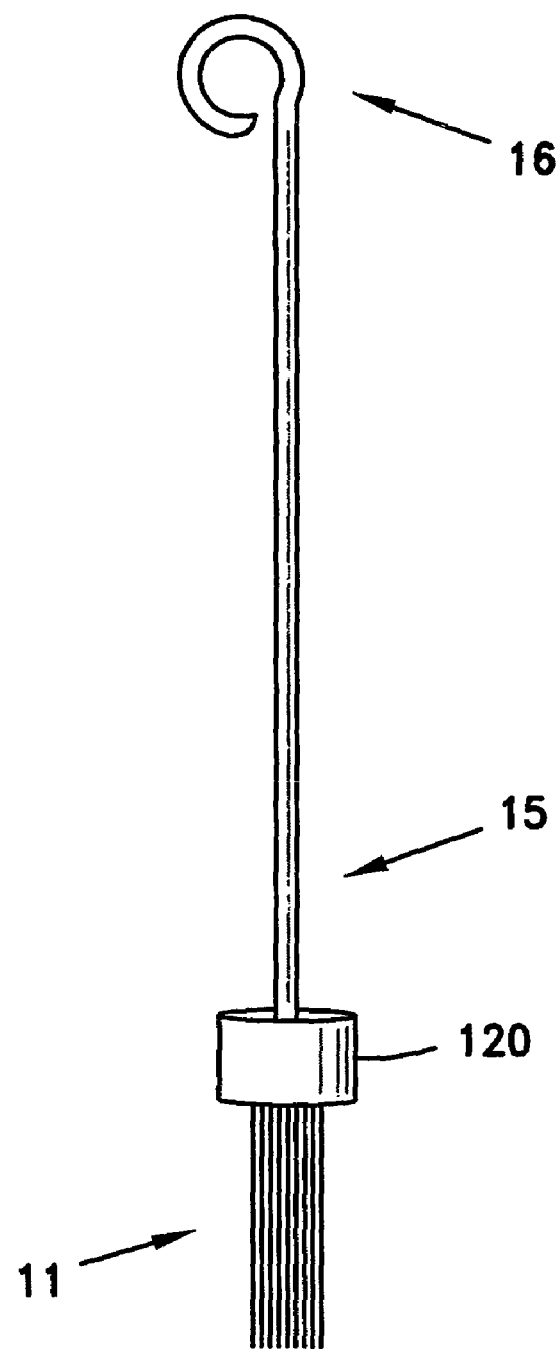
FIGS. 12-14 schematically illustrate an apparatus according to yet another preferred embodiment of the invention.
Figure 13:
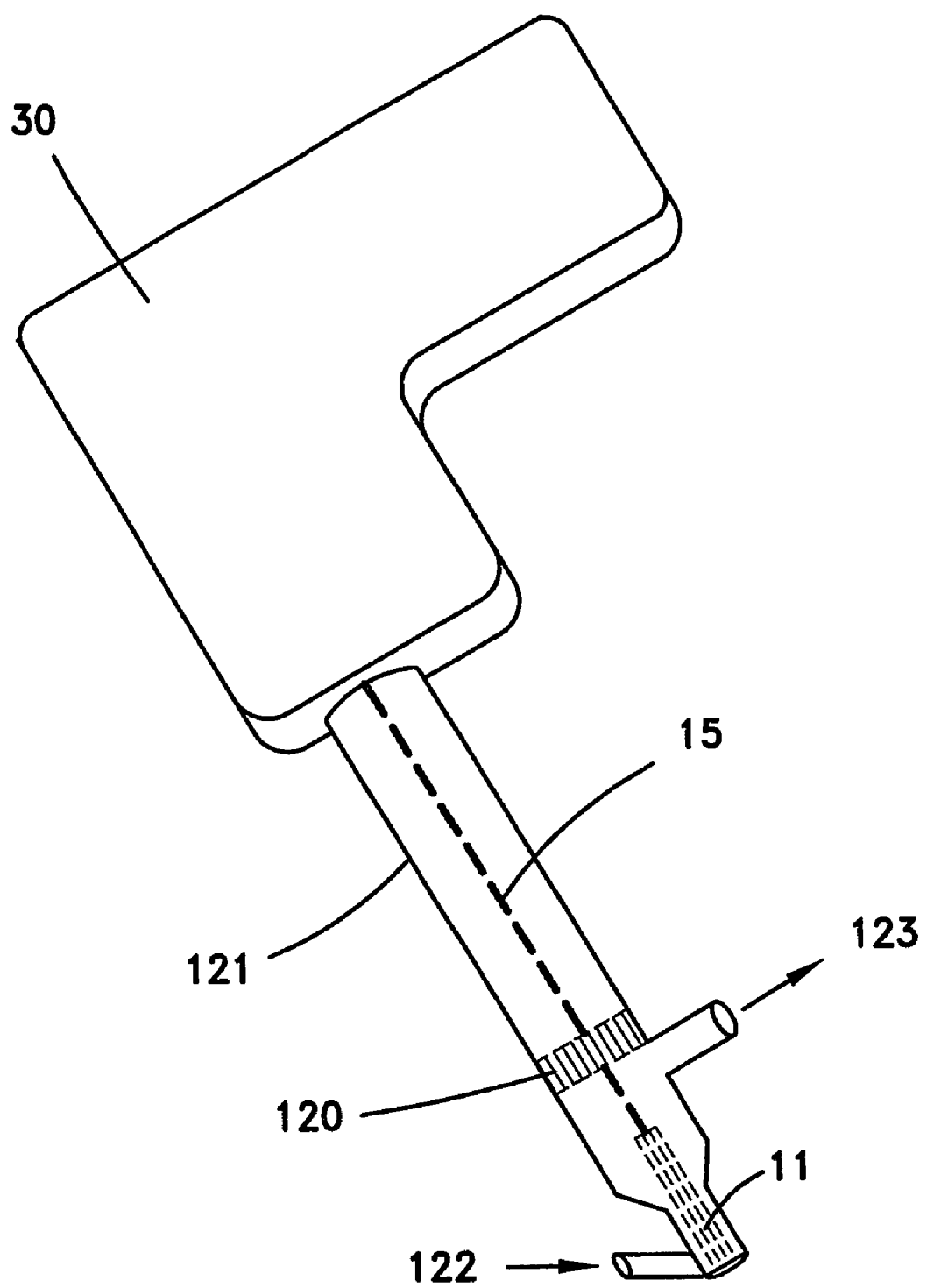
Figure 14:
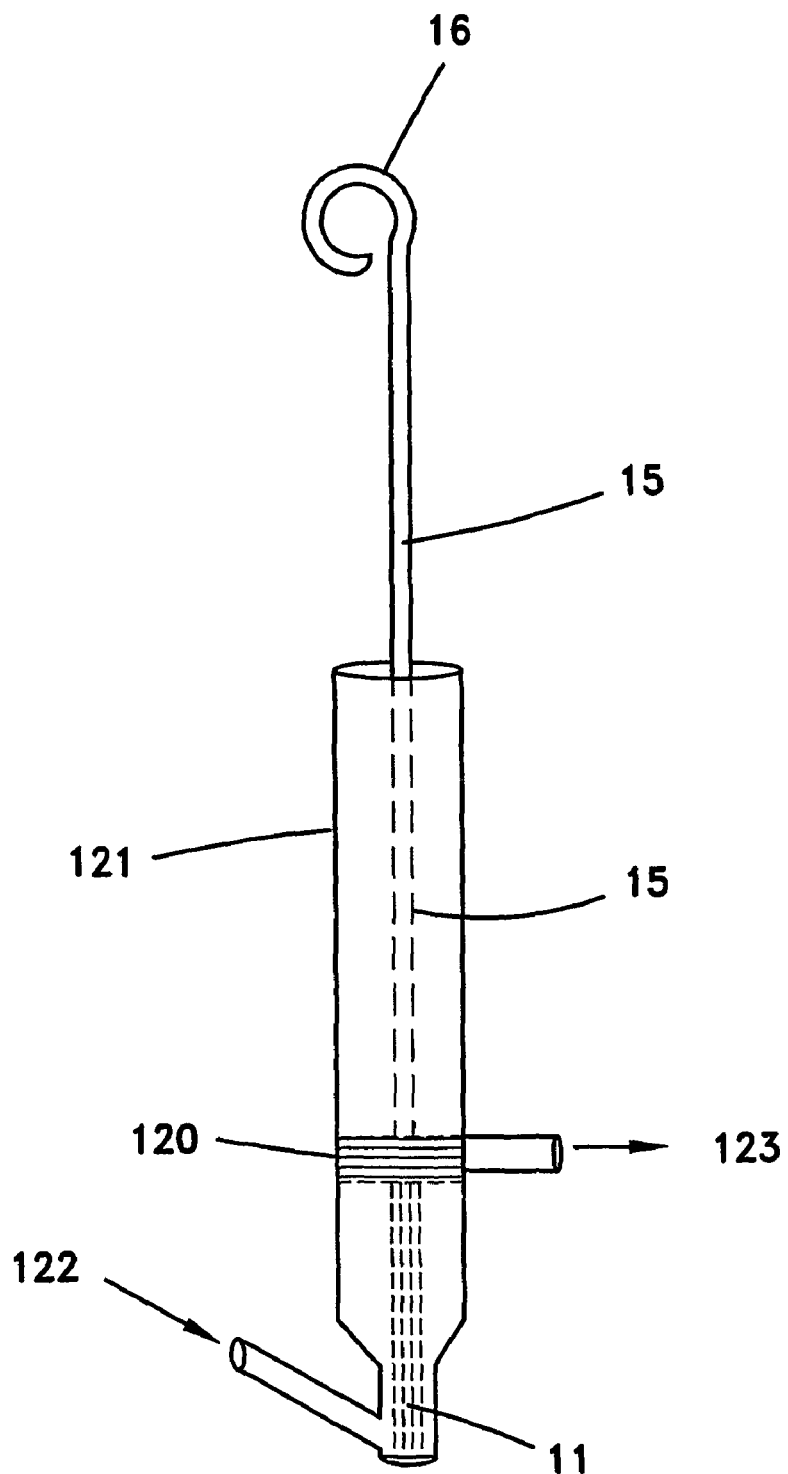

FIGS. 12-14 schematically illustrate an apparatus according to yet another preferred embodiment of the invention. FIG. 12 shows an array of needles of the type shown in FIG. 4, in which the needles are connected to a piston-like member 120, which operates within a cylinder (not shown), as will be further explained with reference to FIG. 13.

In FIG. 13 element 15 is shown in broken lines, with its piston-like element 120 and needles 11, in its inserted position into a cylinder, 121. Cylinder 121 is provided with an inlet 122, for clean fluid to be applied to the area on which operation is taking place, and outlet 123 for the debris and dissolved pigments to be removed therefrom. The vacuum generated by piston-like element 120, displaced within cylinder 121, generates a suction action, as will be apparent to the skilled person, which causes the fluids to be pumped out of the cylinder. In the position shown in FIG. 14, piston-like element 120 closes opening 123. At that stage the empty space around the needle is filled with clear liquid and, when the piston-like element is displaced upwards, the fluid is sucked away. The group of needles located below the piston-like element can contain different numbers of needles. The piston-like element is responsible both for the creation of a vacuum and for the inflowing of liquid into the treated area.

The above examples and description have of course been provided only for the purpose of illustration and are not intended to limit the invention in any way. As will be appreciated by the skilled person, the invention can be carried out in a great variety of ways, employing more than one technique from those described above, all without exceeding the scope of the invention.

What is claimed is:

1. An apparatus for removing pigments from a pigmented section of skin, comprising:
    a) a skin-puncturing device having vibrating means;
    b) an array of one or more needles connected to said skin-puncturing device, each needle of the array having a length of up to 30 mm and adapted for puncturing the skin at said pigmented section, the skin-puncturing device adapted for vibration of said needles such that the needles repeatedly puncture the skin at said pigmented section to create a punctured section of skin, the skin-puncturing device further adapted to enable adjustment of a penetrating depth of said needles into said pigmented section such that said needles penetrate a dermis layer of said skin but do not penetrate a hypodermis layer; and
    c) a mediating member connected to said skin-puncturing device and to a section means, the mediating member adapted to create an essentially isolated area above the punctured section of skin, thereby allowing said suction means to collect a mixture of pigments with cellular fluids at said punctured section of skin and to clean a surface of said punctured section of skin as said skin is repeatedly punctured by said needles.

2. The apparatus according to claim 1, wherein the mediating member comprises one or more openings through which the suction means collects the mixture of pigments with cellular fluids.

3. The apparatus according to claim 1, wherein the mediating member further comprises means for connecting said member to a source of a cleaning material for applying said cleaning material onto the punctured section of skin, thereby cleaning the punctured area during removal of the pigments from the pigmented section of skin.

4. The apparatus according to claim 3, wherein the means for connecting the mediating member to the source of the cleaning material is one or more openings through which cleaning material can be delivered.

5. The apparatus according to claim 2, wherein the mediating member is attached to the skin-puncturing device in such a way that the openings are located adjacent to a sharp edge of the array of needles.

6. The apparatus according to claim 1, wherein said one or more needles are hollow, said hollow needles having openings suitable to be connected to a source of cleaning material for applying said cleaning material onto the punctured section of skin, thereby cleaning the punctured area during removal of pigments from the pigmented section of skin.

7. The apparatus according to claim 3, wherein the cleaning material is a fluid, air under pressure, or a combination of both fluid and air under pressure.

8. The apparatus according to claim 1, wherein the mediating member is attached to the skin-puncturing device with one or more screws.

9. The apparatus according to claim 1, wherein the skin-puncturing device is a tattooing machine.

10. The apparatus according to claim 4, wherein the mediating member is attached to the skin-puncturing device in such a way that the openings are located adjacent to a sharp edge of the array of needles.

11. The apparatus according to claim 1, wherein the isolated area is a sealed cavity above said punctured section of skin.

12. A method for removing pigments from a pigmented section of skin, comprising:
    a) providing an apparatus comprising;
        (i) a skin-puncturing device having vibrating means and including no ink;
        (ii) an array of one or more needles connected to said skin-puncturing device, each needle of the array having a length of up to 30 mm and adapted for puncturing the skin at said pigmented section to create a punctured section of skin,
        (iii) a mediating member connected to said skin-puncturing device, the mediating member adapted to create an essentially isolated area above the punctured section of skin; and
        (iv) a suction means connected to said skin-puncturing device, thereby allowing said suction means to collect a mixture of pigments with cellular fluids at said punctured section of skin, and
    (b) adjusting said skin-puncturing device such that said needles penetrate a dermis layer of skin but do not penetrate a hypodermis layer of skin;
    (c) repeatedly puncturing the skin at said pigmented section with said needles; and
    (d) performing suction, with said suction means, of the mixture of pigments with cellular fluids at said punctured section of skin.

13. A method according to claim 12, further comprising delivering a fluid to the punctured section of skin.

14. A method according to claim 13, wherein the fluid is injected to a section of skin in which pigments are located.

15. A method according to claim 12, further comprising:
    e) providing a pad containing one or more materials capable of absorbing moisture from said mixture of pigments with cellular fluids; and
    f) bandaging said punctured section of skin with said pad, thereby causing pigment residue to migrate from its location toward an outer layer of the skin.

16. A method according to claim 12, further comprising applying fluids onto the punctured section of skin for cleaning said punctured section of skin.

17. A method according to claim 12, further comprising bandaging the punctured section of skin with a pad containing one or more antiseptic materials for preventing infection.

18. A method according to claim 12, wherein the skin-puncturing device is a tattooing machine.

19. A method according to claim 13, wherein the fluid delivered to the punctured section of skin is saline.

* * * * *